United States Patent [19]
Schneider

[11] Patent Number: 4,927,363
[45] Date of Patent: May 22, 1990

[54] DENTAL PROSTHESIS IMPLANT

[75] Inventor: Rudolf Schneider, Heidenreichstein, Austria

[73] Assignee: Metall- u. Kunststoffwaren Erzeugengsgesellschaft M.B.H., Vienna, Austria

[21] Appl. No.: 293,239

[22] Filed: Jan. 4, 1989

[30] Foreign Application Priority Data

Jan. 4, 1988 [AT] Austria ............................. 4/88

[51] Int. Cl.⁵ ........................................... A61C 8/00
[52] U.S. Cl. ................................. 433/173; 433/169
[58] Field of Search ............... 433/169, 173, 174, 175, 433/176

[56] References Cited

U.S. PATENT DOCUMENTS 4,746,293  5/1988  Lundgren et al. ............... 433/169
4,756,689  7/1988  Lundgren et al. ............... 433/169

Primary Examiner—John J. Wilson
Attorney, Agent, or Firm—Herbert Dubno

[57] ABSTRACT

An implant in which a primary member is secured to the bone and has a recess receiving a secondary member. A screw threaded into a threaded bore of the secondary member drives a compression ring against an O-ring to permit the same radially and axially against the primary member to secure the secondary part to the primary part, seal the two relative to one another and allow a releasable connection.

10 Claims, 1 Drawing Sheet

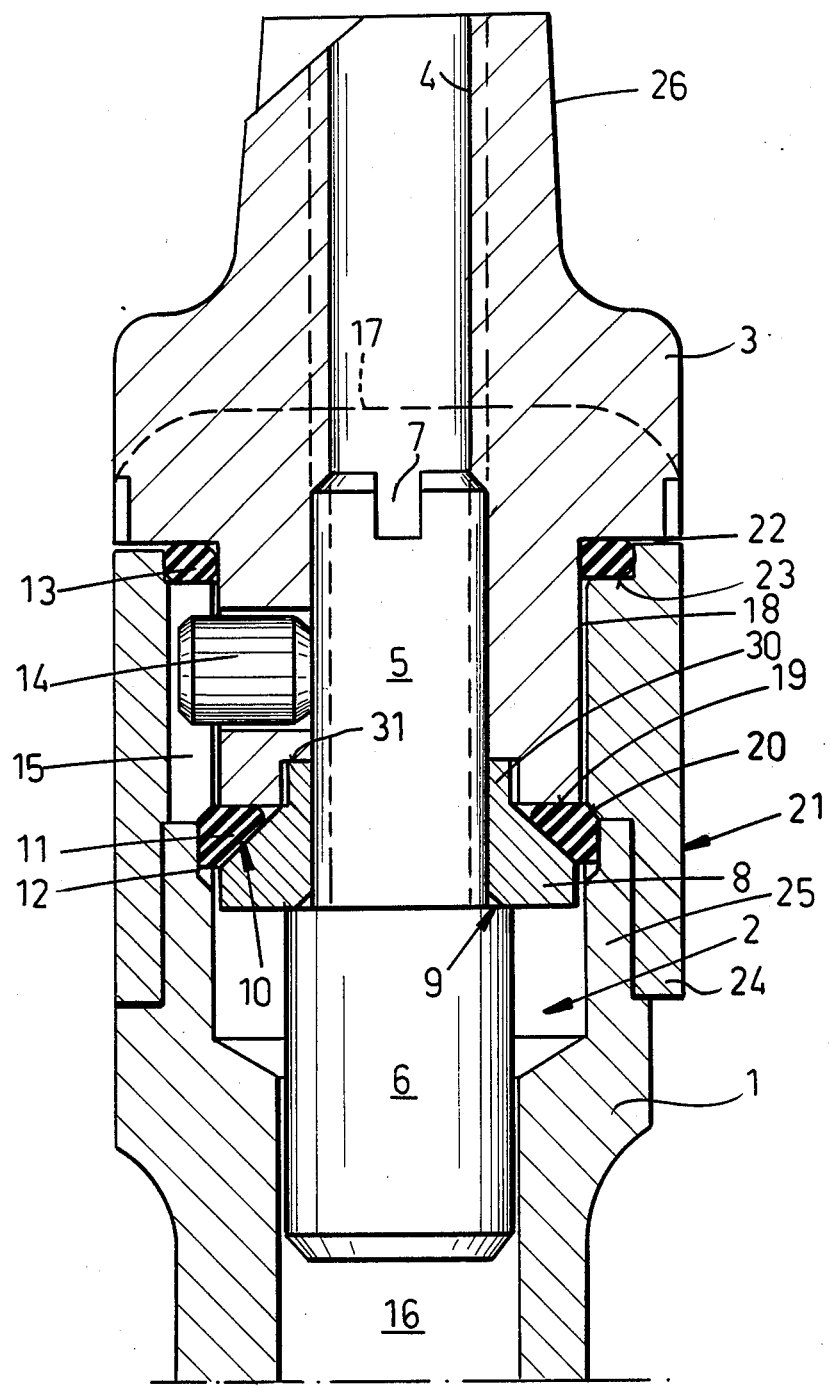

DENTAL PROSTHESIS IMPLANT

CROSS-REFERENCE TO RELATED PATENTS

This application is related to U.S. Pat. No. 4,387,794 issued June 14, 1983 and U.S. Pat. No. 4,553,653 issued Nov. 19, 1985.

1. Field of the Invention

My present invention relates to a dental prosthesis implant and, more particularly, to a two-part implant adapted to secure a dental prosthesis, e.g. a crown or replacement tooth, in the jaw of subject.

2. Background of the Invention

A two-part implants in which a primary part is anchored in a jaw bone and a secondary part can be resiliently engaged with the primary part to allow a certain amount of play similar to the movement permitted in a tooth, can serve to receive a crown or artificial tooth and can make use of an O-ring received in annular grooves of the two parts. Indeed, two such O-rings can be provided and the arrangement can be made so that these O-rings spring into the respective grooves when the secondary part is inserted into the primary part.

The arrangement, of course, has the desired resilience and play, but can pose problems with respect to separation of the secondary part from the primary part, especially if the primary part has not fully been bonded to the bone.

There is also a danger with such systems upon assembly that one or both of the O-rings will be shifted out of position and, as a consequence, make it difficult to seal the junction, cause problems with respect to the resilient support of the secondary part or make it difficult to separate the two.

OBJECTS OF THE INVENTION

It is the principal object of the present invention to provide an improved implant for affixing a dental prosthesis in the mouth of a subject whereby the aforementioned drawbacks are avoided.

Another object of the invention is to provide an implant which can simplify and ease the removal of the secondary part from the primary part, especially where the bone has not fully grown around the primary part to anchor it in place and which also will provide better attachment of the secondary part and better sealing than earlier two-part implants.

SUMMARY OF THE INVENTION

These objects and others which will become apparent hereinafter are attained, in accordance with the present invention, in an implant for affixing a dental prosthesis which comprises:

a primary member anchorable in a jawbone of a subject to be fitted with a dental prosthesis, this primary member having a recess opening at an end of the primary member and formed with an annular wall;

a secondary member detachably connectable to the primary member and formed with a throughgoing axial bore;

a screw in alignment with the bore and provided with a tool-engaging formation enabling rotation of the screw by a tool inserted into the bore;

a compression ring engaged by the screw and displaceable upon rotation of the screw axially toward a surface of the secondary member; and an O-ring clamped between the compression ring and said surface, positioned in the recess and radially compressed against the wall between the surface and the compression ring upon rotation of the screw in one sense to resiliently retain the secondary member on the primary member, the O-ring release from the primary member upon rotation of the screw in a sense opposite the one sense to permit removal of the secondary member from the primary member.

Advantageously, the compression ring is formed with a frustoconical surface diverging in a direction opposite a direction of displacement of the compression ring by rotation of the screw in one sense whereby the O-ring is pressed outwardly and the parts are drawn axially together upon rotation of the screw in one sense.

The secondary member can be formed with a stop surface engaged by the compression ring upon rotation of the screw in the one sense to define a maximum compression of the O-ring.

Thus in accordance with the invention, the secondary part has an axial bore and provides at its end turned toward the primary part a surface against which an O-ring is clamped by rotation of the screw utilizing a screwdriver inserted through the the bore and into the screwdriver slot of the screw, the latter being advantageously tightened until the screw or the compression ring comes to abut a step surface of the secondary part so that the inclined surface of the compression will not only displace the O-ring radially outwardly and provide a force-fit against the inner wall of the recess of the primary part, but so that an axial component of the compression force can serve to draw the primary and secondary parts together.

The O-ring or other elastic sealing ring is thus deformed in the sense of a diameter enlargement in the radial direction after insertion of the secondary part into the primary part.

The deformation and thus the holding force can be set by the screwdriver and its rotation of the screw.

Preferably, the screw is threaded into a threaded portion of the axial bore of the secondary part and the screw has a head or shoulder which is of a larger diameter than this bore so that it radially overlaps the aforementioned end of the secondary part and forms a seat for the compression ring.

The outer diameter of the compression ring is such that the compression ring is received with play in the recess, i.e. the outer diameter is less than the inner diameter of the recess. The compression ring is formed with the inclined surface as described. If the screw is partly threaded into the bore, the O-ring is compressed and the connection made between the primary and secondary parts. As the screw is threaded out of the bore, the compression of the O-ring is released and the O-ring contracts inwardly to terminate the connection and allow ready separation of the secondary part from the primary part.

It has been found to be advantageous to have the primary part form an abutment surface which engages the O-ring when the latter is radially expanded so that the expansion action will allow the O-ring to brace against the primary part in the axial direction and permit the secondary part to be drawn toward the primary part.

This abutment surface can be a part of the annular groove formed in the primary part.

Advantageously, a further O-ring or sealing ring is provided at the mouth of the primary part and sealingly received between the two parts, preferably lying in a groove of the primary part. The secondary part can be juxtaposed with all-around clearance or play with the rim or mouth region of the primary part when the screw is fully tightened.

As a consequence of the drawing of the secondary part into the primary part by tightening of the screw, the secondary part bears sealingly on the further O-ring of sealing ring although a gap between the primary and secondary parts is maintained to ensure a resilient mobility of the secondary part analogous to the tooth mobility.

For especially good retention of the two parts together and guidance of the secondary part with respect to the primary part, it has been found to be advantageous to extend the screw in the axial direction with an elongated nonthreaded head which can be of a larger diameter than the threaded shank and can be received with slight play in the radial direction and with play in the axial direction in a bone of the primary part.

BRIEF DESCRIPTION OF THE DRAWING

The above objects, features and advantages of my invention will become more readily apparent from the following description, reference being made to the accompanying drawing the sole FIGURE of which is an axial cross-sectional view of an implant according to the invention.

SPECIFIC DESCRIPTION

A primary part or member 1 of the implant is intended to be fitted into a hole drilled in a jaw bone in the usual manner and will ultimately be held in place by bone growth. The primary member or part 1 is formed with a central recess 2 and covers a sleeve 21 which may be affixed to the part 1 in any conventional way, e.g. by having its end 24 slid over a boss 25 of the primary part 1. In this case, therefore, the primary member 1 is made up of two parts.

The secondary part 3 which has a boss 26 on which the prosthesis may be formed, is provided with an axial threaded bore 4 in which a screw 5 is threaded. The screw 5 has an enlarged centering head or pin 6 which is not threaded at one end and a screwdriver slot 7 at its opposite end.

A compression ring 8 is seated upon the shoulder 9 between the threaded shank and the centering pin 6 of the screw 5 and moves axially upon rotation of the screw. The compression ring 8 has a frustoconical surface 10 which diverges toward the primary part 1 or converges away from the latter.

Between the inclined surface 10 and an end face or surface 19 of the secondary part 3, an O-ring 11 can be radially compressed. Thus as the screw is tightened into the bore 4 the compression ring 8 is moved upwardly in the orientation of the implant shown to compress the ring 11 against the surface 19. The ring is radially pressed outwardly as well and rests against a wall of an annular groove 12 formed in the recess to the primary part.

The O-ring 11 is elastically deformed and also presses against a seating surface 20 forming part of the annular groove 3, thereby bracing the O-ring so that an axial force component reacts against the compression ring 8 and draws the secondary part or member 3 further into the primary part or member 1.

At the mouth of the primary part 1 formed by the upper end of the sleeve 21, a further sealing ring, namely a further O-ring 13, is provided in a groove 23 and is compressed by the downWard movement of the shoulder 22 of the secondary part 3 as the screw 5 is tightened.

Between the primary part and the secondary part 3, all around the primary part, a slight clearance or play is provided in the form of a gap 18 which permits slight relative movement of the two parts in the sense of natural tooth mobility. In spite of this mobility, the two parts are effectively sealed relative to one another.

Upon a reverse rotation of the screw 5 to displace the screw out of the bore 4, the radial pin 14 is liberated so that it can move out of an axial groove 15 in the inner wall of the sleeve 21 which prevents relative rotation of the parts 1 and 3.

The centering pin or head 6 engages with slight play in a bore 16 of the primary part.

To ensure that there will be a defined retention force between the secondary part 3 and the primary part 1, the screw 5 is tightened until a boss 30 of the compression ring comes to rest against a stop surface 31 of the secondary part 3. Thus the screw can always be fully tightened and will always press the ring 11 outwardly with the same pressing force even if the parts have been separated several times.

To permit such separation, the screw 5 is loosened as described so that the O-ring 20 can contract and relates the radial force applied by it against the primary part.

To provide a permanent growth of the bone around the primary part 1 free from interference, the primary part can be provided with a closure cap 17 shown in broken lines and across which the gum flesh can grow. The cap 17 can be held in place by a screw 5 and sealing rings as described. An undesired loosening can be precluded with certainty, but it is possible to replace the cover 17 with the prosthesis carrying secondary part 3 with ease even if the primary part 1 has not been fully anchored in the bone.

I claim:

1. An implant for affixing a dental prosthesis, comprising:
   a primary member anchorable in a jawbone of a subject to be fitted with a dental prosthesis, said primary member having a recess opening at an end of said primary member and formed with an annular wall;
   a secondary member detachably connectable to said primary member and formed with a throughgoing axial bore;
   a screw in alignment with said bore and provided with a tool-engaging formation enabling rotation of said screw by a tool inserted into said bore;
   a compression ring engaged by said screw and displaceable upon rotation of said screw axially toward a surface of said secondary member; and
   an O-ring clamped between said compression ring and said surface, positioned in said recess and radially compressed against said wall between said surface and said compression ring upon rotation of said screw in one sense to resiliently retain said secondary member on said primary member, said O-ring releasing from said primary member upon rotation of said screw in a sense opposite said one sense to permit removal of said secondary member from said primary member, said compression ring being formed with a frustoconical surface diverging in a direction opposite a direction of displacement of said compression ring by rotation of said screw in said one sense whereby said O-ring is pressed outwardly and said parts are drawn axially together upon rotation of said screw in said one sense, said secondary member being formed with a stop surface engaged by said compression ring upon rotation of said screw in said one sense to define a maximum compression of said O-ring.

2. The implant defined in claim 1 wherein said formation is a screwdriver slot.

3. The implant defined in claim 2 wherein said bore is threaded over at least a portion of the length of the bore, said screw is threaded into said bore and provided within said bore with said slot.

4. The implant defined in claim 3 wherein said screw is formed with a shoulder radially overlapping said secondary part and against which said compression ring is seated.

5. The implant defined in claim 4 wherein said screw is formed with an axial extension beyond said shoulder received with limited clearance in an axial bore formed in said primary part.

6. The implant defined in claim 3 wherein said compression ring is received with all-around clearance in said recess.

7. The implant defined in claim 3 wherein said primary part is formed with an axial bracing surface against which said O-ring bears upon radial compression of said O-ring to force said secondary part toward said primary part.

8. The implant defined in claim 7 wherein said bracing surface is defined by an annular groove formed in said recess.

9. The implant defined in claim 3 wherein said primary part is formed by a plurality of members joined in a region of said groove.

10. The implant defined in claim 3, further comprising another O-ring clamped between said primary and secondary parts upon rotation of said screw in said one sense and spaced axially from the first-mentioned O-ring, said secondary part being received with play in said primary part upon full tightening of said screw in said one sense.

* * * * *